United States Patent
Satzger et al.

(10) Patent No.: US 9,535,012 B2
(45) Date of Patent: Jan. 3, 2017

(54) METHOD FOR THE NON-DESTRUCTIVE TESTING OF WORKPIECE SURFACES

(71) Applicant: MTU Aero Engines AG, Munich (DE)

(72) Inventors: Wilhelm Satzger, Munich (DE);
Joachim Bamberg, Dachau (DE);
Roland Hessert, Herrsching (DE);
Robert Schuster, Munich (DE);
Thomas Hess, Munich (DE)

(73) Assignee: MTU AERO ENGINES AG, Munich (DE)

( * ) Notice: Subject to any disclaimer, the term of this patent is extended or adjusted under 35 U.S.C. 154(b) by 218 days.

(21) Appl. No.: 14/323,183

(22) Filed: Jul. 3, 2014

(65) Prior Publication Data
US 2015/0017736 A1 Jan. 15, 2015

(30) Foreign Application Priority Data
Jul. 9, 2013 (DE) .................. 10 2013 213 369

(51) Int. Cl.
*G01N 21/91* (2006.01)
*G01N 21/33* (2006.01)
*G01N 21/64* (2006.01)

(52) U.S. Cl.
CPC .............. *G01N 21/91* (2013.01); *G01N 21/33* (2013.01); *G01N 21/6447* (2013.01)

(58) Field of Classification Search
CPC G01N 21/91; G01N 2291/0234; G01N 23/18; G01N 33/20; G01N 19/08; Y10S 252/96; C09D 5/22; Y10T 428/12063; B23K 2201/34
See application file for complete search history.

(56) References Cited

U.S. PATENT DOCUMENTS

| | | | |
|---|---|---|---|
| 4,281,033 A | 7/1981 | Mlot-Fijalkowski | |
| 4,641,518 A | 2/1987 | Hutchings | |
| 5,115,136 A | 5/1992 | Tomasch | |
| 5,529,660 A | 6/1996 | Kogan et al. | |
| 8,901,515 B2 | 12/2014 | Bamberg et al. | |
| 2013/0187061 A1 | 7/2013 | Bamberg et al. | |

FOREIGN PATENT DOCUMENTS

| | | |
|---|---|---|
| DE | 3039226 A1 | 4/1982 |
| DE | 3342855 A1 | 6/1985 |
| EP | 0677611 A | 10/1995 |

(Continued)

OTHER PUBLICATIONS

Prat et al.. "Ozone and ozone/UV decoloration of bleaching waters of the paper industry", Ind. Eng. Chem. Res., 1990.*

*Primary Examiner* — Yelena G Gakh
(74) *Attorney, Agent, or Firm* — Abel Law Group, LLP

(57) ABSTRACT

Disclosed is a method for the non-destructive testing of workpiece surfaces of a workpiece by means of fluorescent penetrant testing or dye penetrant testing. The method comprises applying a penetrant to the region of the workpiece surface to be examined, thereby allowing the penetrant to penetrate into possible recesses in the workpiece surface, applying a developer to the region of the workpiece surface to be tested; bleaching the penetrant by a gaseous or liquid oxidant; and visually assessing the penetrant that has remained in the recesses present in the workpiece surface.

19 Claims, 2 Drawing Sheets

(56) References Cited

FOREIGN PATENT DOCUMENTS

| | | | |
|---|---|---|---|
| EP | 0978719 | A1 | 2/2000 |
| EP | 2623963 | A1 | 8/2013 |
| GB | 819925 | A | 9/1959 |
| GB | 2098233 | A | 11/1982 |
| GB | 2109395 | A | 6/1983 |
| JP | S5530618 | A | 3/1980 |
| JP | H03197851 | A | 8/1991 |
| WO | 0170644 | A1 | 9/2001 |

* cited by examiner

METHOD FOR THE NON-DESTRUCTIVE TESTING OF WORKPIECE SURFACES

CROSS-REFERENCE TO RELATED APPLICATIONS

The present application claims priority under 35 U.S.C. §119 of German Patent Application No. 102013213369.3, filed Jul. 9, 2013, the entire disclosure of which is expressly incorporated by reference herein.

BACKGROUND OF THE INVENTION

1. Field of the Invention

The invention relates to a method for the non-destructive testing of workpiece surfaces by means of penetrant testing.

2. Discussion of Background Information

Methods for the non-destructive testing of workpiece surfaces are known. In what is termed penetrant testing, a penetrant is applied to a cleaned workpiece surface which is to be examined. The capillary action of fine surface cracks and pores promotes the penetration of the penetrant into such recesses on the workpiece surface. Dye penetrant testing methods use non-fluorescent dye solutions as the penetrant (e.g. "red-white method"). In what is termed fluorescent penetrant testing, use is made of a fluorescent penetrant. After a predetermined time of action, excess penetrant is then washed away in an intermediate cleaning operation. Then, a developer is applied to the workpiece surface which is to be tested. The developer promotes the re-wetting of the penetrant on the recess in the workpiece surface, the developer causing the penetrant to be drawn out of the recess to the surface. As a result, possible irregularities in the workpiece surface, e.g. crack-like material separations, become clearly visible.

Fluorescent penetrant testing is used in particular in aircraft construction, shipbuilding and automotive engineering and also other metalworking industries. However, it is also possible to examine other materials, e.g. ceramic, for corresponding surface cracks and pores.

However, a disadvantage of the known method, in particular when used in aircraft construction, is that, after the application of the developer and the corresponding mapping of the recesses or surface cracks, to verify the display, the corresponding regions of the presumed recesses have to be subjected to manual surface cleaning in order to remove excess penetrant which has been redistributed on the workpiece surface around the region of the recess by the application of the developer. Only after this mechanical cleaning does the penetrant which lines exclusively the recess or the surface crack become visible. An accurate assessment and measurement of the recess are made possible only in this way. However, this manual cleaning step is time-consuming and costly. Moreover, it can be standardized only with difficulty, as a result of which a standardized classification of possible recesses or defects in the workpiece surface is also difficult.

It would be advantageous to have available a method for the non-destructive testing of workpiece surfaces which makes a quicker and less expensive examination of the workpiece surfaces possible.

SUMMARY OF THE INVENTION

The present invention provides a method according to the invention for the non-destructive testing of workpiece surfaces of workpieces by means of penetrant testing, specifically fluorescent penetrant testing and/or dye penetrant testing. The method comprises the following steps:
(a) cleaning the region of the workpiece surface which is to be examined;
(b) applying a penetrant to the region of the workpiece surface which is to be examined, wherein the penetrant penetrates into possible recesses in the workpiece surface and is a liquid fluorescent penetrant and/or a liquid non-fluorescent dye penetrant;
(c) removing the excess penetrant from the workpiece surface;
(d) applying a developer to the region of the workpiece surface which is to be examined;
(e) bleaching the fluorescent penetrant and/or the non-fluorescent dye penetrant by a gaseous or liquid oxidant in the layer formed by the application of the developer to the workpiece surface; and
f) visually assessing the fluorescent penetrant and/or non-fluorescent dye penetrant which has remained in the recesses present in the workpiece surface.

The bleaching of the fluorescent penetrant and/or of the non-fluorescent dye penetrant in the developer layer makes it possible to dispense with manual cleaning of the workpiece surface after the application of the developer. The corresponding recesses or defects, crack-like material separations, pores and cracks in the workpiece surface are clearly delineated, marked and mapped by the at least partial bleaching of the penetrant which has been drawn out of the corresponding recesses by the developer back to the workpiece surface. The visual assessment is made on the basis of the fluorescent penetrant and/or non-fluorescent dye penetrant which is still in said recesses, and therefore the recesses are clearly delineated with respect to the surrounding workpiece surface. Moreover, some of the penetrant in the recesses is pressed back into the developer layer above and/or alongside the corresponding recesses on account of the osmotic pressure. This advantageously gives rise to a type of magnification effect, which highlights the recesses more clearly and allows them to be recognized. Furthermore, portions of the penetrant which have not accumulated in the recesses but rather adhere to irregularities or foreign bodies on the surface of the workpiece are reliably bleached, and therefore the remaining, unbleached portions of penetrant clearly indicate the presence of recesses. Manual surface cleaning is not required. Advantageously, the method according to the invention can be standardized, and therefore a similarly standardized classification of possible defects or recesses on workpiece surfaces is possible. Moreover, automation of the penetrant testing is possible. The bleaching of the fluorescent penetrant and/or of the non-fluorescent dye penetrant by means of the gaseous or liquid oxidant also reliably eliminates a background fluorescence which possibly arises in the case of workpieces with rough surfaces, and therefore the testing of workpiece surfaces can be carried out easily and reliably. Furthermore, the method according to the invention can be carried out cost-effectively.

In advantageous embodiments of the method according to the invention, the oxidant used is gaseous ozone. In this case, the workpiece with the workpiece surface can be introduced into a chamber or container filled with ozone to carry out method step e). It is also possible that the workpiece with the workpiece surface is exposed to an ozone stream at least in the region of the workpiece surface. Furthermore, it is possible that the workpiece with the workpiece surface is exposed to an oxygen stream and at the same time to intense UV radiation for forming the ozone at least in the region of the workpiece surface to carry out method step e). It has been found that ozone has outstanding suitability as the oxidant for the bleaching operation of the method according to the invention. Other gaseous or liquid oxidants can also be used, these having to ensure complete or virtually complete bleaching of the penetrant in the layer formed by the application of the developer to the workpiece surface. It is also possible that the oxidant is heated to carry out method step e). This advantageously accelerates the bleaching operation considerably.

In an advantageous embodiment of the method according to the invention, a first visual assessment of the workpiece surface is made in a method step (d1) before method step (e), i.e. the bleaching of the fluorescent penetrant and/or of the non-fluorescent dye penetrant. This intermediate step makes it possible to carry out a first visual inspection of possible recesses or defects in the workpiece surface, such that the subsequent bleaching of the fluorescent penetrant and/or of the non-fluorescent dye penetrant concentrates on those regions of the workpiece surface in which possible recesses or defects are identified. This can contribute to a further acceleration of the method sequence.

In further advantageous embodiments of the method according to the invention, the visual assessment as per method step (f) and/or (d1), when using a fluorescent penetrant, can be made by irradiating the workpiece surface to be examined with UV light. Recesses on the workpiece surface which are filled or wetted with the fluorescent penetrant can thereby be clearly identified. A clear and precise visualization of recesses in the workpiece surface is possible owing to the UV radiation used.

In a further advantageous embodiment of the method according to the invention, a further operation for bleaching the fluorescent penetrant and/or the non-fluorescent dye penetrant in the developer layer by means of the gaseous or liquid oxidant can be carried out after or during the visual assessment as per method step (f). As a result, the visual results which have already been obtained can be verified once again.

In a further advantageous configuration of the method according to the invention, the workpiece surface can be cleaned after the conclusion of method step (f), such that the workpiece can be subjected immediately to further processing, in particular a repair method.

In a further advantageous embodiment of the method according to the invention, method steps (b) to (f) can be repeated after the conclusion of method step (f). The repetition of these method steps can advantageously lead to an even more precise mapping of undesirable recesses on the workpiece surface.

In a further advantageous embodiment of the method according to the invention, the workpiece surface is a surface of a turbomachine, in particular of a component of a gas turbine. Components of turbomachines, e.g. of an aircraft engine, are particularly critical in terms of irregularities on the component surfaces, e.g. fine cracks.

In a further advantageous embodiment of the method according to the invention, the penetrant is a fluorescent dye penetrant. Through the use of a fluorescent dye penetrant, a colored configuration of possible recesses in the workpiece surface is also possible in addition to the display of fluorescence. The visual assessment of the corresponding recesses on the workpiece surface can thereby be carried out very easily and precisely.

The above-described method according to the invention is used in particular for the production, for the final testing and for the maintenance of components of a turbomachine, in particular of components of a gas turbine.

BRIEF DESCRIPTION OF THE DRAWINGS

Further features of the invention become apparent from the claims and the exemplary embodiments and also on the basis of the drawings. The features and combinations of features mentioned above in the description and also the features and combinations of features mentioned below in the exemplary embodiments can be used not only in the combination indicated in each case but also in other combinations or on their own, without thereby departing from the scope of the invention. In the drawings:

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1A:
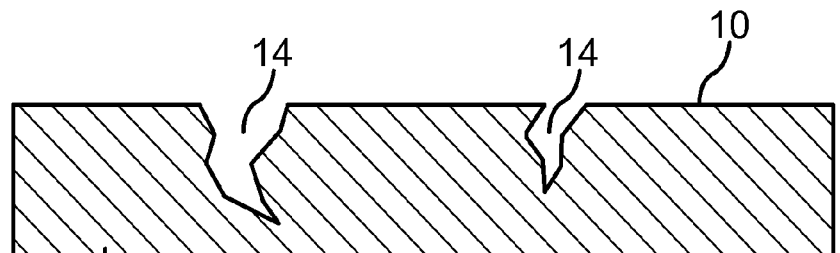
FIGS. 1a to 1f show a sequence of a method according to the invention for the non-destructive testing of workpiece surfaces by means of penetrant testing.
Figure 1B:
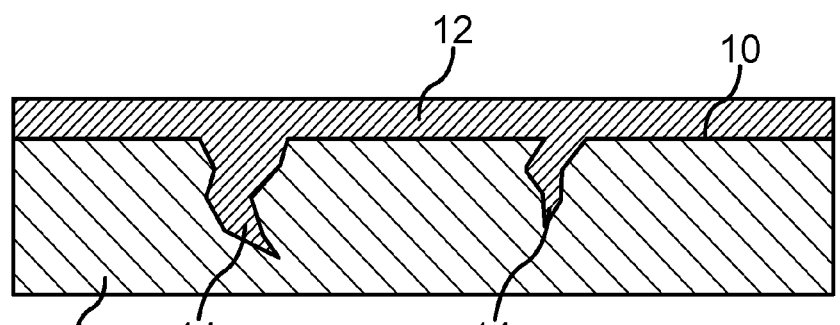
Figure 1C:
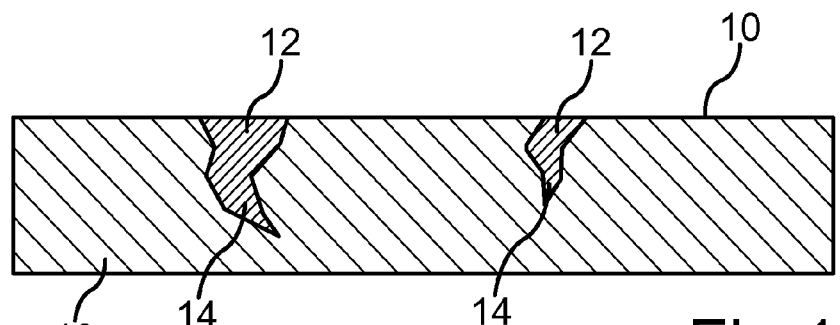
Figure 1D:
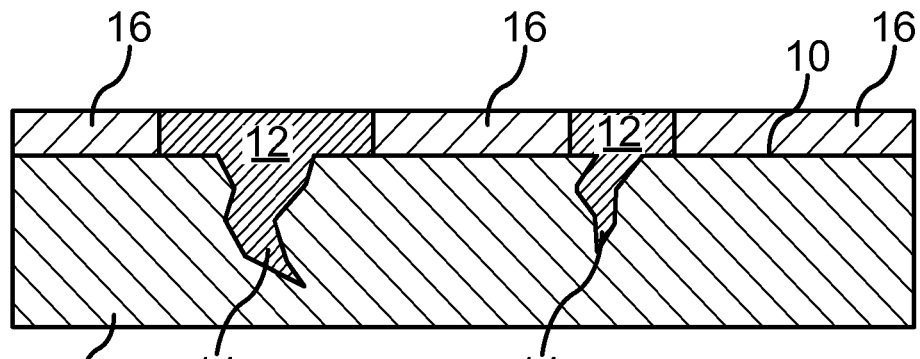

FIGS. 1a to 1f show a sequence of a method for the non-destructive testing of a workpiece surface 10 of a workpiece 18. FIG. 1a shows a workpiece 18 having a workpiece surface 10 and crack-like recesses 14 in the workpiece surface 10. The workpiece surface 10 has been cleaned of impurities. FIG. 1b shows the workpiece 18 with a penetrant 12 applied to the workpiece surface 10. It can be seen that, in addition to the layered application on the workpiece surface 10, the penetrant 12 also penetrates into the crack-like recesses 14. In the exemplary embodiment shown, use is made of a liquid fluorescent penetrant 12. Corresponding fluorescent penetrants 12 are known in large number from the prior art. Use can also be made of other, non-fluorescent penetrants. In this respect, depending on the type and material of the workpiece 18 to be examined, it is necessary to use penetrants 12 which, on account of their specifically set properties, each have the tendency not only to spread out on the workpiece surface 10 but also at the same time to penetrate into the corresponding recesses 14 in the workpiece surface 10. In this respect, it is possible to use penetrants 12 based on hydrocarbons and organic dyes.

After a penetration time which is specific to the penetrant 12, excess penetrant 12 is removed from the workpiece surface 10 in a subsequent method step. The cleaned and dried workpiece surface 10 can be seen in FIG. 1c. The penetrant 12 is still present only in the recesses 14. In a further method step, a developer 16 is then applied to the region of the workpiece surface 10 which is to be tested. The application of the developer 16 causes the penetrant 12 to be drawn out of the recess 14 back to the workpiece surface 10. It becomes clear from FIG. 1d that now the penetrant 12 is present not only in the recess 14, but also within the developer layer 16 in the regions on the workpiece surface 10 which surround the recess 14.

Figure 1E:
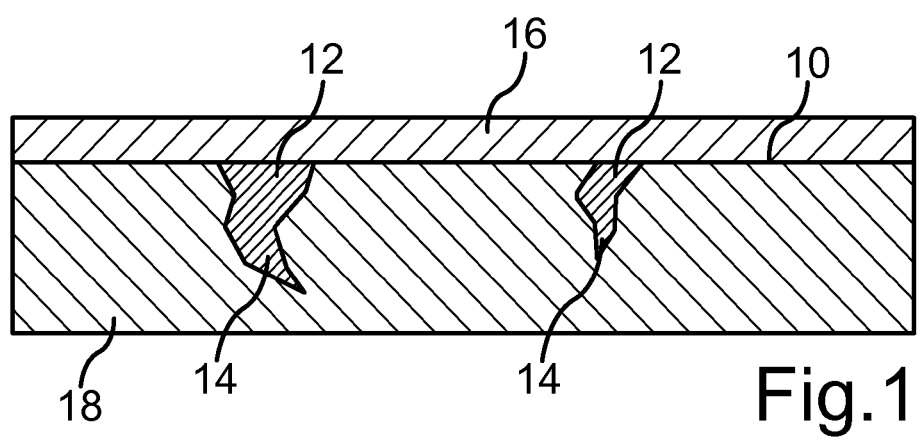

In a subsequent, further method step, the fluorescent penetrant 12 within the layer formed by the application of the developer 16 to the workpiece surface 10 is then bleached by means of the application of gaseous ozone or the introduction of the workpiece 18 with the workpiece surface 10 into a gaseous ozone environment. The bleaching is performed until achieving at least partial and even complete bleaching of the fluorescent components within the penetrant 12 in the layer of the developer 16. FIG. 1e shows the end of the bleaching operation with complete bleaching of the fluorescent components of the penetrant 12 within the developer layer 16. The developers 16 used are likewise known from the prior art, with use commonly being made of inorganic substances in powder form.

Figure 1F:
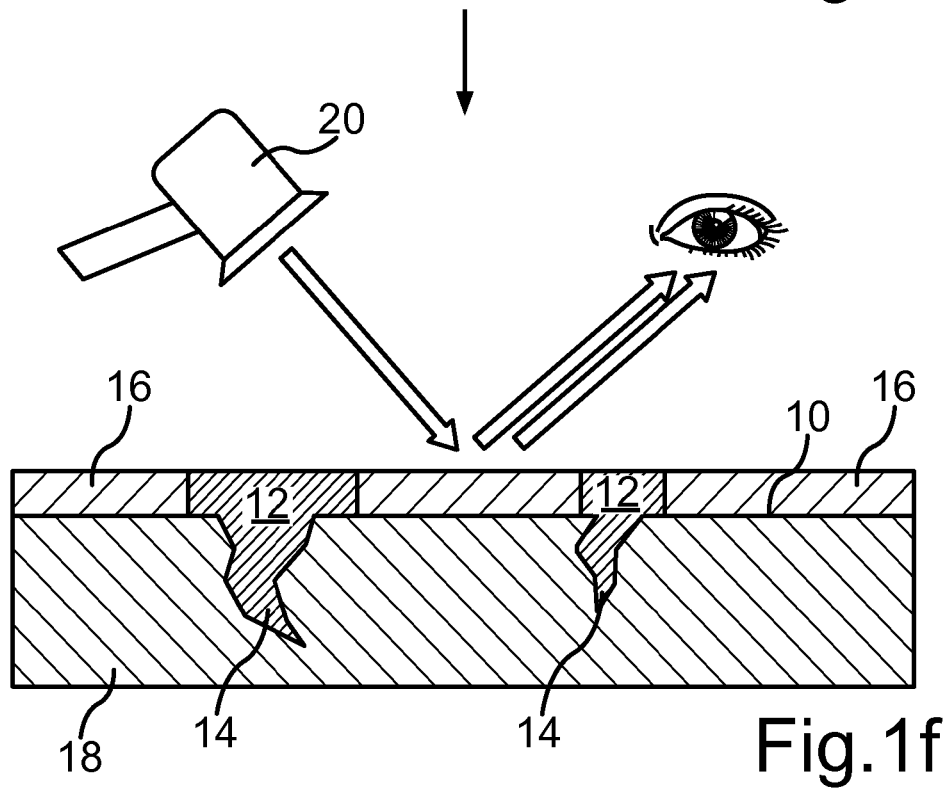

FIG. 1f shows a final method step, specifically the visual assessment of the fluorescent penetrant 12 which has remained in the recesses 14 present in the workpiece surface 10. On account of the preceding bleaching operation, the fluorescent penetrant 12 is predominantly still located only within the crack-like recesses 14 and no longer on irregularities or foreign bodies on the workpiece surface 10. The edges of the crack-like recesses 14 are marked and can accordingly be observed and assessed. Moreover, some of the penetrant 12 in the recesses 14 is pressed back into the developer layer 16 above and/or alongside the recesses 14 on account of the osmotic pressure. This advantageously gives rise to a type of magnification effect, which highlights the recesses 14 more clearly and allows them to be recognized.

Moreover, the bleaching operation shown in FIG. 1e eliminates background fluorescence which is possibly present, and therefore the fluorescent markings or regions which denote the crack-like recesses 14 are clearly identifiable. The following advantages in particular are achieved by the method described: a precisely defined bleaching operation which can be automated, no mechanical distortion of the measurement results and the possibility of repeated verification of the method.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for the non-destructive testing of a workpiece surface of a workpiece by fluorescent penetrant testing or dye penetrant testing, wherein the method comprises:
   (a) cleaning a region of the workpiece surface which is to be examined;
   (b) applying a liquid fluorescent penetrant or a liquid non-fluorescent dye penetrant to the region of the workpiece surface which is to be examined, thereby allowing the penetrant to penetrate into possible recesses in the workpiece surface;
   (c) removing excess penetrant from the workpiece surface;
   (d) applying a developer to the region of the workpiece surface which is to be examined and from which excess penetrant has been removed;
   (e) bleaching the penetrant by a gaseous or liquid oxidant in a layer formed by applied developer on the workpiece surface; and
   (f) visually assessing penetrant that has remained in the recesses present in the workpiece surface.

2. The method of claim 1, wherein the oxidant comprises ozone.

3. The method of claim 2, wherein in (e) the workpiece with the workpiece surface is introduced into a chamber or container filled with ozone.

4. The method of claim 2, wherein in (e) the workpiece with the workpiece surface is exposed to an ozone stream at least in a region of the workpiece surface.

5. The method of claim 2, wherein in (e) the workpiece with the workpiece surface is exposed to an oxygen stream and at the same time to UV radiation for forming the ozone at least in a region of the workpiece surface.

6. The method of claim 2, wherein (b) to (f) are repeated after conclusion of (f).

7. The method of claim 1, wherein in (e) the oxidant is heated.

8. The method of claim 1, further comprising (d1) a first visual assessment of the workpiece surface prior to (e).

9. The method of claim 8, wherein in (d1) the workpiece surface to be examined is irradiated with UV light.

10. The method of claim 1, wherein in (f) the workpiece surface to be examined is irradiated with UV light.

11. The method of claim 1, wherein a further operation for bleaching the fluorescent penetrant or the non-fluorescent dye penetrant in a developer layer by the gaseous or liquid oxidant is carried out after or during the visual assessment of (f).

12. The method of claim 1, wherein (b) to (f) are repeated after conclusion of (f).

13. The method of claim 1, wherein the workpiece surface is a surface of a turbomachine.

14. The method of claim 1, wherein the workpiece surface is a surface of a component of a gas turbine.

15. The method of claim 1, wherein the penetrant comprises a fluorescent dye penetrant.

16. The method of claim 1, wherein the penetrant comprises a non-fluorescent dye penetrant.

17. A method for the production of a component of a turbomachine, wherein the method comprises carrying out the method of claim 1.

18. The method of claim 1, wherein the workpiece surface is a surface of a component of a gas turbine.

19. A method for the maintenance of a component of a turbomachine, wherein the method comprises carrying out the method of claim 1.

* * * * *